United States Patent [19]

Kigasawa et al.

[11] Patent Number: 4,500,511
[45] Date of Patent: Feb. 19, 1985

[54] ANTIINFLAMMATORY AND ANALGESIC GEL

[75] Inventors: Kazuo Kigasawa; Hideaki Ohtani, both of Tokyo; Toshiyuki Kanezuka, Kawasaki, all of Japan

[73] Assignee: Grelan Pharmaceutical Co., Ltd., Tokyo, Japan

[21] Appl. No.: 531,745

[22] Filed: Sep. 13, 1983

[30] Foreign Application Priority Data

Sep. 14, 1982 [JP] Japan ................. 57-158938

[51] Int. Cl.³ .................. A61U 31/19; A61U 31/78
[52] U.S. Cl. ........................ 424/81; 514/555
[58] Field of Search .................. 424/81, 317

[56] References Cited

U.S. PATENT DOCUMENTS 3,763,229  10/1973  Noguchi et al. ............... 260/515 A
4,309,414   1/1982  Inagi et al. ..................... 424/78

OTHER PUBLICATIONS

Chem. Abst., vol. 95—(1981), 103322x.

Primary Examiner—Stanley J. Friedman
Attorney, Agent, or Firm—Wegner & Bretschneider

[57] ABSTRACT

An antiinflammatory and analgesic gel composition for external use which comprises 0.03 to 1.5 percent by weight of clidanac or a pharmacologically acceptable salt thereof as a pharmacologically active ingredient and 0.5 to 5.0 percent by weight of gelling agent, 0.3 to 4.0 percent by weight of a neutralizer, 30 to 60 percent by weight of a solubilizer and 35 to 65 percent by weight of water, has an excellent antiinflammatory and analgesic effect.

9 Claims, No Drawings

ANTIINFLAMMATORY AND ANALGESIC GEL

This invention relates to an antiinflammatory and analgesic gel composition for external use which contains clidanac as a pharmacologically active ingredient.

Clidanac, 6-chloro-5-cyclohexylindane-1-carboxylic acid, has excellent antiinflammatory and analgesic activities and so far has been used as an antiinflammatory and analgesic agent for internal use. The use of clidanac in an external preparation has not been proposed or suggested.

Generally, the epidermis constitutes an immense obstacle against extraneous organic compounds, such as drugs, preventing their permeation or absorption. Therefore, all drugs that are well absorbable through the digestive tract wall when administered internally are not always absorbable through the epidermis. The amount of a drug which is absorbable through the epidermis into a living body is very small as compared with that which is absorbable through the digestive tract, so that, in the prior art, it is required to administer a drug in the form of an external preparation in a dose by far higher than that of the same drug in the form of an oral preparation.

The present inventors, keeping the above problem in mind, conducted their intensive research and development work to make up an external preparation containing, as a pharmacologically active ingredient, clidanace with unknown percutaneous absorbability. As a result, they found that, when incorporated in a specific gel composition and applied to the epidermis, clidanac or a pharmacologically acceptable salt thereof, namely the pharmacologically active ingredient, can be well absorbed percutaneously and can efficiently penetrate into tissues and consequently can produce a marked effect at a dose level as low as about one tenth that of conventional nonsteroidal antiinflammatory and analgesic agents while retaining an effective tissue concentration for a prolonged period of time. The present invention has been completed on the above finding.

Thus, the present invention relates to: an antiinflammatory and analgesic gel composition for external use which comprises 0.03 to 1.5 percent by weight of clidanac or a pharmacologically acceptable salt thereof as a pharmacologically active ingredient and 0.5 to 5.0 percent by weight of a gelling agent, 0.3 to 4.0 percent by weight of a neutralizer, 30 to 60 percent by weight of a solubilizer and 35 to 65 percent by weight of water. The afore-mentioned gel composition is one capable of presenting a gel-like appearance as a whole and holding clidanac or a pharmacologically acceptable salt thereof stably from the pharmaceutical viewpoint and at the same time capable of releasing the pharmacologically active ingredient upon application of the preparation.

The above-mentioned pharmacologically acceptable salt of clidanac includes alkali metal salts (e.g. sodium and potassium salts) and further aluminum, zinc and ammonium salts and salts with organic amines. Among them alkali metal salts are preferable. Clidanac or such a pharmacologically acceptable salt thereof is incorporated in the external preparation in an amount (as clidanac) of 0.03 to 1.5 percent by weight, preferably 0.05 to 1.0 percent by weight.

The afore-mentioned gelling agent includes those polymers that can gel in an alcohol-water system. Examples are carboxyvinyl polymer having an average molecular weight of about 40,000 to about 3,000,000 [e.g. HIVISWAKO 103, 104 or 105 (trademark; Wako Pure Chemical Industries, Japan; described in Wako's Technical Bulletin "HIVISWAKO" issued in 1976) which are crosslinked acrylic polymers, CARBOPOL 934, 940 or 941 (trademark; B. F. Goodrich Chemical; described in Annotated Standards for Cosmetics Ingredients, First Edition, Supplement, pages 58–66, Yakuji Nippo Sha, Japan, 1971), LUVISKOL L-180, K-90 or K-30 (trade mark; Badische Anilin & Soda Fabrik) which are sodium polyacrylates], polyvinyl alcohol, cellulose derivative having an average molecular weight of about 13,000 to about 194,000 (e.g. carboxymethylcellulose, lower hydroxyalkylcellulose such as hydroxymethylcellulose, hydroxyethylcellulose, hydroxypropylcellurose) and alginic acid propylene glycol ester. The gelling agent is used usually in an amount of 0.5–5.0 percent by weight relative to the gel composition, preferably in an amount of 1.0 to 3.0 percent by weight.

The afore-mentioned solubilizer includes, among others, glycols (e.g. low molecular glycols having 3 to 6 carbon atoms such as propylene glycol, butylene glycol, dipropylene glycol, etc., polyethylene glycols having an average molecular weight of about 200 to about 400), lower alcohols having 2 to 6 carbon atoms (e.g. ethanol, denatured ethanol, isopropanol), salicyl glycolate, crotamiton (crotonyl-N-ethyl-o-toluidine) and propylene carbonate. For attaining the purpose of their use, the solubilizer is used usually in an amount of 30 to 60 percent by weight relative to the gel composition, preferably in an amount of 35 to 50 percent by weight.

The neutralizer is used to neutralize the gelling agent and includes, among others, organic amines and alkali hydroxides (e.g. sodium hydroxide, potassium hydroxide). Preferred are organic amines such as lower di- and tri- alkanolamines (e.g. diisopropanolamine, triethanolamine), alanine and ammonia. Such a neutralizer is added usually in an amount of 0.3 to 4.0 percent by weight relative to the gel composition, preferably in an amount of 0.5 to 2.5 percent by weight, so as to adjust the pH of the whole external preparation according to the present invention to neutrality or the proximity thereof, preferably pH 5.5 to 8.0.

The gel composition of the present invention may further contain one or more optional components together with the afore-mentioned essential component. The optional components are usually contained in the present composition in an amount not more than 15 percent by weight.

As optional component, an absorption promoter may be contained in the gel composition. The absorption promoter includes, among others, mono- or di-carboxylic acid alkyl esters (e.g. monocarboxylic acid alkyl ester comprising an carboxylic acid moiety having 4 to 30 carbon atoms, preferably 4 to 18 carbon atoms, and an ester moiety having 1 to 30 carbon atoms, preferably 1 to 20 carbon atoms, such as octyl dodecyl myristate, ethyl laurate, etc., dicarboxylic acid alkyl ester comprising an carboxylic acid moiety having 4 to 20 carbon atoms, preferably 4 to 10 carbon atoms, and two ester moieties, each ester moiety is one having 1 to 20 carbon atoms, preferably 1 to 3 carbon atoms, such as diisopropyl adipate, diethyl sebacate, etc.), salicyclic acid and salts thereof, AZON (trademark; Nelson Research and Development; 1-n-dodecylazacycloheptan-2-one) and urea. For promoting absorption of active components, such absorption promoter is used usually in an amount of 0.3 to 10 percent by weight, relative to the gel base, preferably in an amount of 0.5 to 5.0 percent by weight. As the optional component, a perfume such as menthol, camphor, etc. may further be contained in the gel composition in an amount of not more than 1 percent by weight. Further, as the optional component, pharmacologically active components other than clidanac, such as antiinflammatory and analgesic agents (e.g. methyl salicylate, glycol salicylate), rubefacients (e.g. capsicum extract) and crude drugs or crude drug components (e.g. aloe extract), may also be contained in addition to clidanac or a pharmacologically acceptable salt thereof.

The external preparation according to the present invention is produced, for instance, by adding a suspension or solution of clidanac or a salt thereof in a mixture of a solubilizer and if desirable, an absorption promoter, to a gelling agent swollen in water, stirring the mixture, adding a solution of a neutralizer in water, and then allowing the whole mixture to gelate while stirring.

The thus-obtained external preparation according to the present invention is little irritating to the skin. When applied, it does not feel sticky but feels comfortable. It is highly stable so that it can tolerate long-term storage testing and accelerated testing. The external preparation according to the present invention is administered to mammals such as humans, dogs, horses, rats, mice, rabbits and monkeys. Thus, it is used, for instance, to relieve the pain associated with rheumatism, osteoarthritis, lumbago, tendinitis, peritendinitis, humeroscapular periarthritis, traumatic or nontraumatic acute inflammation or gout in humans. The dose may be increased or decreased in an adequate manner depending on the symptom and the site of disease, among others. For instance, in the case of osteoarthritis, which is said to be hardly curable in the field of orthopedics, the external preparation according to the present invention, when the clidanac content is 0.5 percent by weight, is applied to the back in a dose of 1.0 to 1.5 grams per adult human two to four times per day for consecutive 14 days. In a clinical trial performed in said manner of dosing, an efficacy rate exceeding 80% was obtained.

The following description comprising examples of the antiinflammatory and analgesic preparation for external use in accordance with the present invention and results of tests therewith illustrates the present invention in more detail. Table 1 shows exemplary formulations of the external preparation according to the present invention. The reference examples are given to illustrate the preparations used as controls in the tests. The test examples are given to demonstrate the utility of the antiinflammatory and analgesic preparations according to the present invention as obtained in the corresponding examples.

EXAMPLE 1

The formulation shown in Table 1 was used. (1) HIVISWAKO 104 and HEC were swollen in 30 g of water. (2) Clidanac was dissolved in a mixture of BG, DIPA and ethanol. (3) The solution (2) was added to the above (1), and the mixture was stirred until complete hydration. (4) DIA dissolved in 10 g of water was added to the avove (3), the remaining portion of water was then added, and the whole mixture was stirred until it became homogeneous. There was thus obtained the contemplated external preparation [hereinafter referred to as preparation (A)].

EXAMPLE 2

According to the formulation shown in Table 1 and in the same manner as in Example 1 except that HEC was not used, the contemplated external preparation [hereinafter referred to as preparation (B)] was obtained.

EXAMPLE 3

The formulation shown in Table 1 was used. (1) HIVISWAKO 104 was swelled in 30 g of water. (2) Clidanac was dissolved in a mixture of PG and ethanol. (3) The solution (2) was added to the above (1), and the mixture was stirred until complete hydration. (4) A solution of DIA in 10 g of water was added to the above (3), the remaining portion of water was then added, and the whole mixture was stirred until it became homogeneous. There was thus obtained the contemplated external preparation [hereinafter referred to as preparation (C)].

TABLE 1

| | Exemplary formulations for the external preparation according to the present invention | | | | | | | | |
|---|---|---|---|---|---|---|---|---|---|
| | Example | | | | | | | | |
| Ingredient | 1 | 2 | 3 | 4 | 5 | 6 | 7 | 8 | 9 |
| Clidanac | $0.1^{(g)}$ | $0.1^{(g)}$ | $0.1^{(g)}$ | $0.25^{(g)}$ | $0.5^{(g)}$ | $0.5^{(g)}$ | $0.5^{(g)}$ | $1.0^{(g)}$ | $0.05^{(g)}$ |
| HIVISWAKO 104 | 0.9 | 1.5 | 1.5 | 1.0 | 0.7 | 1.5 | 0.9 | 1.0 | 0.7 |
| H E C | 0.7 | | | 1.0 | 0.7 | | 0.7 | | 0.7 |
| B G | 12.0 | 12.0 | | | | | 12.0 | | |
| P G | | | 12.0 | 12.0 | 12.0 | 12.0 | | 12.0 | 12.0 |
| D I A | 0.7 | 0.7 | 1.6 | 1.4 | 0.8 | 1.8 | 0.9 | 1.4 | 1.5 |
| D I P A | 2.0 | 2.0 | 2.0 | 2.0 | 1.5 | 2.0 | 2.0 | 2.0 | 0.8 |
| Ethanol | 30.0 | 30.0 | 20.0 | 30.0 | 30.0 | 30.0 | 30.0 | 40.0 | 30.0 |
| Purified water | Sufficient quantity to make 100 g | | | | | | | | |

Notes:
H E C = hydroxyethylcellulose;
B G = 1,3-butylene glycol;
P G = propylene glycol;
D I A = diisopropanolamine;
D I P A = Diisopropyl adipate.
In Example 8, 0.01% of l-menthol was further added as a perfume.
In Example 7, clidanac sodium salt was used in place of clidanac.

EXAMPLE 4

According to the formulation shown in Table 1 and by following the procedure of Example 1 but using PG in place of BG, there was obtained the contemplated external preparation [hereinafter referred to as preparation (D)].

EXAMPLE 5

According to the formulation shown in Table 1 and by following the procedure of Example 1 but using PG in place of BG, there was obtained the contemplated external preparation [hereinafter referred to as preparation (E)].

EXAMPLE 6

According to the formulation shown in Table 1 and by following the procedure of Example 3, there was obtained the contemplated external preparation [hereinafter referred to as preparation (F)].

EXAMPLE 7

According to the formulation shown in Table 1 and by following the procedure of Example 1, there was obtained the contemplated external preparation [hereinafter referred to as preparation (G)].

EXAMPLE 8

According to the formulation shown in Table 1 and by following the procedure of Example 3, there was obtained the contemplated external preparation [hereinafter referred to as preparation (H)].

EXAMPLE 9

The contemplated external preparation [hereinafter referred to as preparation (I)] according to the formulation shown in Table 1 was obtained by proceeding in the same manner as in Example 5 except that the clidanac content was varied.

REFERENCE EXAMPLE 1

An absorptive ointment was prepared according to the formulation and method of production as described in the Japanese Pharmacopeia, tenth edition (hereinafter abbreviated to JP X). Clidanac (0.5 g) was uniformly dispersed in 99.5 g of the absorptive ointment. [The resulting preparation is hereinafter referred to as preparation (a).] The absorptive ointment was composed of the following: 40 g of white petrolatum, 18 g of cetanol, 5 g of sorbitan sesquioleate, 0.5 g of LAUROMACROGOL, 0.1 g of ethyl para-hydroxybenzoate, 0.1 g of butyl parahydroxybenzoate and purified water in a sufficient quantity to make 100 g.

REFERENCE EXAMPLE 2

1% Indomethacin ointment (trademarked IDOMETHANE KOWA, Kowa) [hereinafter referred to as preparation (b)] as purchased from the market.

REFERENCE EXAMPLE 3

5% Bufexamac cream [trademarked ANDERM, Lederle (Japan)] [hereinafter referred to as preparation (c)] as purchased from the market.

REFERENCE EXAMPLE 4

Clidanac (1 g) was homogeneously suspended in 99 g of a gum arabic solution. [The resulting solution is hereinafter referred to as preparation (d)]. This preparation was used for oral administration.

REFERENCE EXAMPLE 5

A clidanac-free preparation was prepared in the same manner as in Example 5 using the formulation of Example 5 but without the use of clidanac. [The preparation is hereinafter referred to as preparation (e).]

TEST EXAMPLE 1

Stability testing

Metal tubes or laminated plastic tubes were filled with the preparations obtained in Examples 1 and 5 and Reference Example 1 [preparations (A), (E) and (a)]. After 60 days of storage at a temperature of 40° C. and a humidity of 75% or 90%, the contents were taken out and tested for changes in appearance and consistency and assayed for clidanac content to give the results mentioned below. In assaying clidanac, a certain amount of each preparation was taken out and the clidanac content was determined by high performance liquid chromatography (HPLC) of the extract therefrom using a working curve. The HPLC conditions were as follows: apparatus—Waters model ALC 200-6000, column—$\mu$ Bondapak $C_{18}$, mobile phase—80% acetonitrile solution containing 1/160 M $KH_2PO_4$, rate of flow—1.5 ml/min., detection—UV (284 nm) (detector: Nippon Bunko model UVIDEC 100-II), temperature—room temperature. Under these conditions, clidanac was assayed by injecting 10 $\mu$l of the extract itself into the apparatus.

(1) Appearance and consistency: The gel base external preparations according to the present invention [preparations (A) and (E)] showed no changes either in appearance or in consistency, whereas preparation (a) underwent phase separation of base constituents with time and finally lost its homogeneity entirely.

(2) Percent clidanac content based on the amount of clidanac initially incorporated:
For preparation (A), 98.8%
For preparation (E), 98.9%
For preparation (a), 98.3%

As can be seen from the above data, each base of preparations (A) and (E) can hold clidanac stably. However, the base for the control preparation (a) was questionable in its stability and therefore was not used in the subsequent test examples.

TEST EXAMPLE 2

Suppression of increment of vascular permeability

To the clipped back of Slc-SD strain male rats (weighing 170 to 210 g; in groups of 8 animals), there was administered within the area of 12 $cm^2$ (3×4 cm) 0.1 ml of 0.1% $\lambda$—carrageenin solution by intradermal injection, followed by application of 300 mg of each of the external preparations according to the present invention [preparations (A) and (E)] and the control external preparations [preparations (b), (c) and (e)] to the area of 12 $cm^2$ (3×4 cm). Immediately thereafter, 0.5% Pontamine sky blue was injected into the caudal vein and three hours later the area of dye-leakage (major axis × minor axis) was measured. The results are shown in Table 2.

TABLE 2

| | Suppression of increment of vascular permeability of dye | | |
|---|---|---|---|
| Group | Number of animals | Area of dye leakage (mm²) | Inhibition (%) |
| $(X_1)$ | 8 | 135.8 | — |
| (A) | 8 | 76.9 | 43.4 |
| (E) | 8 | 62.2 | 54.2 |
| (b) | 8 | 67.6 | 50.2 |
| (c) | 8 | 90.2 | 33.6 |
| (e) | 8 | 124.8 | 8.1 |

In the above table, (A), (E), (b), (c) and (e) indicate the respective external preparations applied and $(X_1)$ indicates the non-drug-treated group (control group) in which the carrageenin treatment alone was performed.

It was revealed that the external preparations according to the present invention are rather more potent in the suppression of dye leakage at lower active ingredient content levels as compared with the control external preparations.

TEST EXAMPLE 3

Granuloma pouch method

The back of Slc-SD strain male rats (weighing 180 to 200 g; in groups of 7 to 10 animals) was clipped. Air (25 ml) was injected subcutaneously into the back of the animals and further 0.5 ml of 1% croton oil in sesame oil was injected into the air pouch. The air was removed 48 hours later and the test external preparations [200 mg each of the external preparations according to the present invention (D) and (E) once a day, or 200 mg each of the control external preparations (b) and (e) twice a day] were applied to the area of 12 cm$^2$ (3×4 cm) on the pouch for consecutive five days or the suspension preparation (d) was orally administered once a day in a clidanac dose of 1 mg/kg for 5 days. On the day following the last application (or oral administration), the animals were sacrificed after body weight measurement, and the volume of the fluid exudate in the pouch was measured and the adrenal, spleen and thymus were weighed. The gastrointestinal tract was also observed for possible lesions. The results obtained are shown in Table 3.

As can be understood from Table 3, the external preparations according to the present invention produce excellent effects in low concentrations and by less frequent application. Thus, among the above dosed groups, only those treated with the external preparations according to the present invention gave statistically significant results as compared with the control group. Furthermore, as can be seen in Table 3, any abnormalities worth mentioning were not observed in the organ weight measurement, examination of the gastrointestinal tract and so on, except that gastrointestinal lesions were found in some animals in the oral administration group. This suggests that the external preparations according to the present invention can produce beneficial pharmacological effects without those adverse effects (infrequent digestive tract disorders, etc.) possibly produced by the oral preparation.

TEST EXAMPLE 4

Adjuvant arthritis method

An adjuvant solution of 0.3 mg mycobacterium butylicum in 0.05 ml of liquid paraffin was subcutaneously injected into the right hind paw of Slc-SD strain male rats (weighing 150 to 180 g; in groups of 8 animals). Starting 14 days after injection, 200 mg each of the external preparations (A) and (E) according to the present invention, 200 mg each of the control external preparations (b), (c) and (e) or the suspension preparation (d) (in a dose of 2 mg/kg) was applied to the site of swelling on the left hind paws or orally administered once a day for consecutive 14 days. The site of application was covered for protection with KUREWRAP (trademark; Kureha Chemical Industry) and a surgical tape for 6 hours daily after each application. The foot volume and body weight measurements were made before injection of the adjuvant solution and before application of each test preparation, and, after the start of application, daily.

The results obtained are shown in Table 4, Table 5 and Table 6.

TABLE 4

| Percent (%) inhibition swelling* | |
|---|---|
| Test preparation | Site of Measurement Uninjected foot (left hind paw) |
| External preparation according to the present invention (A) | 46.0 |
| External preparation according to the present invention (E) | 51.9 |
| Control external preparation (b) | 45.2 |
| Control external preparation (c) | 32.9 |
| Oral preparation (d) | 31.0 |

*Percent inhibition on the 14th day of application (or oral administration) of the test preparation as compared with the untreated (control) group.

TABLE 5

Changes in swelling of the left hind paw (Uninjected foot) in Adjuvant arthritis method

| Group | Number of animals | Changes in swelling of left hind paw (Uninjected paw) (%) | | | | | |
|---|---|---|---|---|---|---|---|
| | | 14th day | 16th day | 19th day | 22nd day | 25th day | 28th day |
| (X$_3$) | 8 | 100 | 139.7 | 200.7 | 199.6 | 226.6 | 208.4 |
| (e) | 8 | 100 | 126.9 | 151.1 | 163.0 | 169.9 | 186.2 |
| (A) | 8 | 100 | 84.9 | 81.7 | 101.9 | 95.7 | 112.5 |
| (E) | 8 | 100 | 98.8 | 93.4 | 88.0 | 92.6 | 100.3 |
| (b) | 8 | 100 | 75.4 | 92.4 | 96.6 | 102.3 | 114.3 |

TABLE 3

Experimental results of the croton oil granuloma ponch method*

| Group | Dose (mg/kg) | Number of animals | Body weight gain (g) | Fluid exudate mean value (ml) | Fluid exudate inhibition (%) | Organ weight mg/100 g-body weight | | | Digestive tract disorders Number of animals having disorder | Digestive tract disorders Mean number of ulcer |
|---|---|---|---|---|---|---|---|---|---|---|
| | | | | | | adrenal | apleen | thymus | | |
| (X$_2$) | — | 10 | 30.4 | 5.00 ± 0.46 | — | 11.2 | 161.6 | 236.9 | 0/10 | 0 |
| (D) | about 2.0 | 7 | 29.2 | 3.30 ± 0.37 | 35.8* | 11.5 | 151.8 | 237.6 | 0/7 | 0 |
| (E) | about 4.0 | 7 | 29.0 | 2.81 ± 0.31 | 45.3** | 10.0 | 158.9 | 243.9 | 0/7 | 0 |
| (b) | about 8.0 × 2 | 7 | 33.4 | 4.04 ± 0.34 | 21.8 | 10.3 | 167.3 | 225.7 | 0/7 | 0 |
| (d) | 1.0 | 8 | 30.4 | 3.86 ± 0.24 | 24.9 | 11.1 | 180.2 | 253.7 | 4/8 | 3.6 |
| (e) | — | 10 | 31.4 | 5.14 ± 0.84 | −2.8 | 11.6 | 148.8 | 220.5 | 0/10 | 0 |

Note
*Statistical significancy:
*P < 0.05.
**P < 0.01
(X$_2$) shows the values of the untreated (control) group.

TABLE 5-continued

Changes in swelling of the left hind paw (Uninjected foot) in Adjuvant arthritis method

| Group | Number of animals | Changes in swelling of left hind paw (Uninjected paw) (%) | | | | |
|---|---|---|---|---|---|---|
| | | 14th day | 16th day | 19th day | 22nd day | 25th day | 28th day |
| (c) | 8 | 100 | 111.4 | 156.1 | 146.8 | 147.1 | 139.8 |
| (d) | 8 | 100 | 100.8 | 148.9 | 144.2 | 145.0 | 143.8 |

TABLE 6

Changes in body weight in Adjuvant arthritis method

| Group | Number of animals | Body weight at the start of application (g) (14th day) | Changes in body weight after the 14th day (g) | | | | |
|---|---|---|---|---|---|---|---|
| | | | 16th day | 18th day | 22nd day | 24th day | 28th day |
| ($X_4$) | 8 | 293.5 | 2.8 | 8.3 | 17.2 | 24.7 | 36.0 |
| ($X_3$) | 8 | 242.6 | −7.6 | −8.0 | −10.4 | −8.8 | −1.5 |
| (e) | 8 | 250.1 | −4.6 | −5.0 | −5.8 | 1.5 | 0.4 |
| (A) | 8 | 246.3 | −6.3 | −5.8 | −4.6 | −0.9 | 2.4 |
| (E) | 8 | 251.8 | −7.0 | −5.8 | −1.6 | 2.0 | 11.3 |
| (b) | 8 | 245.5 | −7.9 | −6.8 | −9.8 | −6.3 | −1.3 |
| (c) | 8 | 250.6 | −8.3 | −9.8 | −13.3 | −13.8 | −5.3 |
| (d) | 8 | 248.0 | −9.0 | −9.8 | −8.1 | −5.8 | −5.0 |

From the results of the above experiment, it is understood that the external preparations according to the present invention exhibit higher therapeutic effect in spite of their lower active ingredient concentrations, hence smaller doses than the control external preparations and the oral preparation, and that they produce the highest inhibitory effect on the body weight decrease in adjuvant-treated animals as compared with the control drugs.

TEST EXAMPLE 5

Randall & Selitto's method

A 10% brewer's yeast suspension was injected into the right hind paw of Slc-SD strain male rats (weighing 80 to 100 g; in groups of 10 animals) and thereafter 100 mg of each test external preparation was applied to the same site. The pressure thresholds for pain response were determined before drug application and 1, 2 and 3 hours after application using an electrically driven pressure apparatus. The results obtained are shown in Table 7.

TABLE 7

% Rise in pain threshold of inflamed foot

| Group | Time of measurement | | |
|---|---|---|---|
| | 1 hr | 2 hrs | 3 hrs |
| External preparation according to the invention (A) | 61.8 | 46.4 | 25.0 |
| External preparation according to the invention (E) | 21.8 | 50.2 | 39.5 |
| Base gel (e) | 33.3 | 31.2 | 16.6 |
| Control external preparation (b) | 17.1 | 35.5 | 45.2 |
| Control external preparation (c) | 50.6 | 42.6 | 18.0 |

In the above tables, (A), (E), (b), (c), (d) and (e) indicate the respective preparations applied, ($X_3$) indicates the non-drug-treated group in which the adjuvant treatment alone was performed, and ($X_4$) indicates the the group in which neither the adjuvant treatment nor the drug administration was performed (normal control group).

From the results of the above test, it is seen that the external preparations according to the present invention even in low active ingredient concentrations, produce their pain-relieving effect as reflected by rise in the pain threshold already 1 hour after application, the effect reaching a maximum about 2 hours after application with a rise in the threshold of 50.2%. On the other hand, with the control external preparations, the effect tended either to appear slowly or to be not lasting.

TEST EXAMPLE 6

Tests on percutaneous absorption and in vivo behavior (1) Test external preparations and method of administration Normal human males (aged 44 to 48 years old and weighing 53.5 to 62.5 kg; in groups of 3 individuals) were used. The external preparation (H) according to the present invention was applied to the back (area: 30×40 cm$^2$) in a dose of 5 g/person (containing 50 mg of clidanac). The preparation (H) was also applied to the back (area: 20×25 cm$^2$) in a dose of 2 g/person (containing 20 mg of clidanac). The control external preparation (b) was applied to the back (area: 30×30 cm$^2$) in a dose of 10 g/person (containing 100 mg of indomethacin). In each case, the preparation applied was removed 8 hours after application.

(2) Method of measurement

Following the above application of test preparations, the plasma and urine levels of clidanac and 4 metabolites thereof ($M_1$, $M_2$, $M_3$ and $M_4$) were determined by gas chromatography at timed intervals (2, 4, 6, 12, 24, 36, 48, 72 and 96 hours after application).

The plasma level measurement was performed in the following manner: The plasma (1 ml) was extracted with a benzene-n-heptane mixture under acidic conditions and the organic layer was then extracted with diluted sodium hydroxide. The aqueous layer was washed with butyl acetate, then made acidic, and extracted with benzene. The extract was evaporated to dryness. To the residue were added trichloroethanol and anhydrous trifluoroacetic acid, and the mixture was heated at 75° C. for 10 minutes and then again evaporated to dryness. An internal standard was added to the residue and the resulting mixture was used as the test sample.

The urinary excretion was measured in the following manner: 1 ml of urine was extracted with a benzene-n-heptane mixture under acidic conditions. The solvent was distilled off from the organic layer. To the residue was added phosphate buffer (pH 5.7), the mixture was extracted with benzene, and the organic layer was extracted with diluted sodium hydroxide. The aqueous layer was made acidic and again extracted with benzene, and the extract was evaporated to dryness. The residue was dissolved in ethyl acetate and developed on the thin layer plate (Merck, silica gel 60 F$_{254}$) (solvent: acetonitrile-acetic acid-water=6000:11:9). The layer portions respectively corresponding to clidanac and metabolites thereof ($M_1$ to $M_4$) were collected and extracted with methanol. Each residue obtained upon removal of the methanol was converted to the trichloroethyl ester in the same manner as above mentioned. The test sample thus obtained was used for assaying the unchanged clidanac. The conjugates were converted to the unchanged clidanac by treatment with diluted hydrochloric acid under heating and each product was treated in the same manner as above to give the test sample.

A Shimadzu model 4BM ECD-GC was used as the gas chromatograph, with a 0.2% Poly I-110/Chromosorb W HP column. The column temperature was 205° C. or 210° C., and the $N_2$ flow rate was 20 or 60 ml/min.

(3) Pharmacokinetics in plasma

The plasma level of the unchanged clidanac was measured at timed intervals for the above test external preparations (H) and (b) to give the results shown in Table 8. From the results, it is understood that the external preparation according to the present invention is very good in percutaneous absorbability of clidanac and the disappearance of blood clidanac is very slow as compared with the control external preparation.

(4) Urinary excretion

For the test external preparation (H), the urinary levels of the unchanged clidanac and metabolites thereof ($M_1$, $M_2$, $M_3$ and $M_4$) were measured at timed intervals. The results obtained are shown in Table 9. From the results, it is confirmed that the external preparation according to the present invention allows the presence of not only the unchanged clidanac but also active metabolites thereof in the organism for a prolonged period of time. This supports high and lasting activity of clidanac.

was treated with 2,2,2-trichloroethanol in the presence of $BF_3$-ether, and the resulting ester was used as the test sample and assayed for clidanac by ECD gas chromatography as mentioned in Test Example 6. The indomethacin assay was performed according to the method of Arbin. [Journal of Chromatography, vol. 144, page 85 ff, (1971)].

(3) Results and discussion

For comparative evaluation of the test external preparations with respect to percutaneous absorbability, the area under the serum concentration-time curve for the 24-hour period after application was determined for each dose level as the bioavailability parameter. The results obtained are shown in Table 10.

As can be seen in Table 10, the external preparations give higher AUC (area under the serum concentration-time curve) values than those for the indomethacin ointment. It is thus understood that said external preparations are superior in percutaneous absorbability of active ingredient to said ointment. With the external preparation (H) according to the present invention, the serum level of clidanac 24 hours after application was 218 ng/ml. This value is higher than that for the indomethacin ointment (80 ng/ml). It has thus been revealed that the external preparations according to the present

TABLE 8

Changes in the concentration of the unchanged clidanac in the human plasma

Concentration of clidanac in human plasma (mg/ml)

| Group | Dose | 2 hours later | 4 hours later | 6 hours later | 8 hours later | 12 hours later | 24 hours later | 36 hours later | 48 hours later | 66 hours later | 72 hours later | 96 hours later |
|---|---|---|---|---|---|---|---|---|---|---|---|---|
| (H) | 2 g | 13.3 | 22.3 | 24.0 | — | 43.4 | 76.9 | 73.5 | 70.1 | — | 60.4 | 52.9 |
| (H) | 5 g | 31.4 | 35.3 | 48.4 | — | 83.4 | 100.8 | 143.6 | 128.5 | — | 92.5 | 70.5 |
| (b) | 10 g | 6.8 | 12.6 | 20.2 | 13.4 | 12.8 | 7.2 | — | 1.4 | 1.1 | — | — |

TABLE 9

Urinay excretion amount of clidanac and metabolites thereof ($M_1$–$M_4$) (μg/ml)*

| Group | Time | Unchanged clidanac | metabolites of clidanac | | |
|---|---|---|---|---|---|
| | | | $M_1 + M_2$ | $M_3$ | $M_4$ |
| (H) 2 g | 0–24 | 29.4 | 18.3 | 39.1 | 57.3 |
| | 24–48 | 30.3 | 31.5 | 74.3 | 79.0 |
| | 0–48 | 59.8 | 49.8 | 113.4 | 136.3 |
| (H) 5 g | 0–24 | 31.8 | 38.8 | 58.5 | 107.7 |
| | 24–48 | 46.7 | 81.8 | 123.8 | 174.9 |
| | 0–48 | 78.5 | 119.9 | 182.3 | 282.6 |

*Urinary excretion amount is shown total amount of free clidanac and conjugated clidanac

TEST EXAMPLE 7

Experiment on percutaneous absorption (1) Test external preparation and method of administration The external preparations (I), (A), (F) and (H) each according to the present invention were applied in clidanac doses of 1, 2, 10 and 20 mg/body to the clipped back of male albino rabbits (weighing 2.5 to 2.9 kg; in groups of 5 animals) within the area of $8 \times 10$ cm$^2$. In a further group, the control external preparation (b) was applied in indomethacin doses of 2, 10 and 20 mg/body.

(2) Assay method

The serum was separated, made acidic with hydrochloric acid and extracted with cyclohexane, and the organic layer was washed with water and then extracted with 0.5 N sodium hydroxide. The extract was made acidic and extracted with benzene. The solvent was distilled off from the benzene layer. The residue invention, once absorbed percutaneously, are eliminated from the organism much more slowly, hence retained therein much longer.

TABLE 10

AUC (area under the serum concentration-time-curve)
(Administration 0–24 hours)

| Group | Dose (mg/8 × 10 cm$^2$) | AUC μg/ml · hr |
|---|---|---|
| (H) | 20 | 12.01 |
| (F) | 10 | 7.88 |
| (A) | 2 | 3.62 |
| (I) | 1 | 2.23 |
| (b) | 20 | 7.88 |
| (b) | 10 | 4.24 |
| (b) | 2 | 0.82 |

REFERENCE EXAMPLE 6

Following the procedure of Examples 1, 4, 5 and 8 but using the same amounts of indomethacin in place of clidanac, the following preparations were prepared:

Preparation (f): The procedure of Example 1 was followed using 0.1 g of indomethacin in place of 0.1 g of clidanac;

Preparation (g); The procedure of Example 4 was followed using 0.25 g of indomethacin in place of 0.25 g of clidanac;

Preparation (h): The procedure of Example 5 was followed using 0.5 g of indomethacin in place of 0.5 g of clidanac;

Preparation (i): The procedure of Example 8 was followed using 1 g of indomethacin in place of 1 g of clidanac.

TEST EXAMPLE 8

Suppression of increased vascular permeability (1) Method

The hair on the back of Hartley strain albino guinea pigs (male; weighing 235 to 270 g; in groups of 7 animals) was removed with an electric hair clipper and an electric razor, circles, 2.5 cm in diameter (4.91 cm$^2$ in area), were drawn symmetrically on both sides of the medium line, and 50 mg of each test external preparation was applied to the area of each circle. Three hours after application, 0.1 ml of 0.1% λ-carrageenin solution was injected intradermally into the center of each circle, followed by injection of 0.5 ml/100 g of body weight of 0.5% Pontamine sky blue solution into the vein of the penis. Three hours after injection, each animal was sacrificed by decapitation, exsanguinated and flayed, and the area of dye leakage (major axis x minor axis) on the inner side of the skin was measured with slide calipers.

The external preparations used were preparations (A), (D), (E) and (H) containing of 0.1%, 0.25%, 0.5% and 1% of clidanac, respectively, and preparations (f), (g), (h) and (i) containing 0.1%, 0.25%, 0.5% and 1% of indomethacin, respectively. In the control group, any preparation was not administered but massage alone was performed.

For further comparison, oral preparations respectively containing clidanac and indomethacin were prepared by the procedure of Reference Example 4 and orally administered in a clidanac dose of 2 mg/kg and in an indomethacin dose of 2 mg/kg, respectively, and the animals were treated in the same manner as mentioned above.

The rate of suppression was calculated using the follwoing formula:

$$\% \text{ Suppression} = \frac{C - T}{C} \times 100 \, (\%)$$

where C is the area of dye leakage for the control group and T is the area of dye leakage for the drug-treated group.

(2) Results and discussion

The results obtained in the above test are shown in Table 11.

As can be understood from Table 11, clidanac and indomethacin, when administered orally, were almost equivalent in effect, whereas when administered percutaneously, the external preparation according to the present invention containing 0.1% of clidanac already displayed statistically significant suppressive effect but the 1% indomethacin-containing external preparation alone displayed a significant difference as compared with the control group. In this manner, the external preparations according to the present invention can produce excellent effects in low active ingredient concentrations.

TABLE 11

Suppression of increment of vascular permeability*

| Group | Active ingredient Concentration (%) | Dose (mg/kg) | Area of dye leakage (mm$^2$) | Suppression rate (%) |
|---|---|---|---|---|
| Control group | — | 0 | 234.6 ± 19.0 | |
| Oral administration group | 1.0 | 2.0 | 193.8 ± 12.1 | 17.4* |
| Indomethacin | 1.0 | 2.0 | 195.7 ± 13.6 | 16.6* |
| Test external preparation groups | | | | |
| Clidanac | | | | |
| (A) | 0.1 | 0.2 | 187.8 ± 14.3 | 19.9* |
| (D) | 0.25 | 0.5 | 170.7 ± 19.6 | 27.2* |
| (E) | 0.5 | 1.0 | 152.1 ± 9.5 | 35.2** |
| (H) | 1.0 | 2.0 | 139.6 ± 8.0 | 40.5** |
| Indomethacin | | | | |
| (f) | 0.1 | 0.2 | 211.8 ± 25.5 | 9.7 |
| (g) | 0.25 | 0.5 | 217.5 ± 18.3 | 7.3 |
| (h) | 0.5 | 1.0 | 201.8 ± 10.7 | 14.0 |
| (i) | 1.0 | 2.0 | 188.6 ± 13.6 | 19.6* |

*The active ingredient concentration indicates the w/w concentration of clidanac or indomethacin in each preparation, and the dose is indicated in terms of the dose of clidanac or indomethacin.
* and ** mean statistical significancy; *, $p < 0.05$; **, $p < 0.01$.

TEST EXAMPLE 9

Ultraviolet erythema method (1) Method

The hair on the back of Hartley strain albino guinea pigs (male; weighing 240 to 250 g; in groups of 7 animals) was removed with an electric clipper and an electric razor, a thin black rubber sheet (provided with six small holes, 6.5 mm in diameter, in isolation from one another but concentratedly within a circle 4 cm in diameter) was fixedly applied to the clipped site. After irradiation with a mercury lamp (power consumption 600 watts; wavelengths 250–260 nm; Toshiba Iryo-yohin K.K.) from a distance of 14.5 cm for 3 minutes, the above rubber sheet was removed and 62.8 mg of a test external preparation [each of preparations (E) and (H) containing 0.5% and 1% of clidanac, respectively and preparations (h) and (i) containing 0.5% and 1% of indomethacin, respectively] was applied. Two hours after application, the external preparation was wiped off with alcohol. Erythema was scored 2, 3, 4 and 5 hours after application according to the criteria: score 1.0—erythema distinctly noted in the form of a circle; score 0.5—slight erythema noted in part; score 0—no erythema. The scores for the 6 holes were totalled for each guinea pig. The scoring of erythema was performed by a third party in the manner of a blind test. In the control group, the preparation of Reference Example 5, namely preparation (e), consisting of a gel base alone was used in place of the above test external preparations.

(2) Results and discussion

The results of the above test are shown in Table 12.

As can be understood from Table 12, the external preparations according to the present invention displayed statistically significant erythema-suppressing effect as compared with the control group at any time of observation. They are thus decidedly superior to the indomethacin-containing preparations.

TABLE 12

Changes in the erythema score in Ultraviolet erythema method

| Group | Number of animals | Erythema score | | | |
|---|---|---|---|---|---|
| | | 2 hours later | 3 hours later | 4 hours later | 5 hours later |
| (e) | 7 | 5.40 | 3.90 | 3.80 | 4.90 |
| (E) | 7 | 0.08 | 0.83 | 1.17 | 1.50 |
| (H) | 7 | 0.05 | 0.66 | 0.82 | 1.05 |
| (h) | 7 | 1.40 | 2.64 | 2.94 | 3.15 |
| (i) | 7 | 1.08 | 2.00 | 2.67 | 2.92 |

What is claimed is:

1. An antiinflammatory and analgesic gel composition for extermnal use which comprises 0.03 to 1.5 percent by weight of clidanac or a pharmacologically acceptable salt thereof as a pharmacologically active ingredient and 0.5 to 5.0 percent by weight of a gelling agent, which is at least one selected from the group consisting of a carboxyvinyl polymer, a cellulose derivative and an alginic acid propylene glycol ester, 0.3 to 4.0 percent by weight of a neutralizer, 30 to 60 percent by weight of a solubilizer and 35 to 65 percent by weight of water.

2. A gel composition as claimed in claim 1, wherein the gel composition is one further including 0.3 to 10 percent by weight of an absorption promoter.

3. A gel composition as claimed in claim 1, wherein the pharmacologically active ingredient is clidanac.

4. A gel composition as claimed in claim 1, wherein the pharmacologically acceptable salt of clidanac is an alkali metal salt, aluminum salt, ammonium salt or an organic amine salt.

5. A gel composition as claimed in claim 1, wherein the pharmacologically acceptable salt is an alkalimetal salt.

6. A gel composition as claimed in claim 1, wherein the gelling agent is a carboxyvinyl polymer.

7. A gel composition as claimed in claim 1, wherein the solvilizer is a glycol, a lower alcohol or propylene carbonate.

8. A gel composition as claimed in claim 1, wherein the neutralizer is an alkalimetal hydroxide or an organic amine.

9. A gel composition as claimed in claim 2, the absorption promoter is a mono- or di-carboxylic acid alkyl ester, salt thereof, 1-n-dodecyllazacycloheptan-2-on or urea.

* * * * *